(12) United States Patent
Bruton et al.

(10) Patent No.: US 7,846,922 B2
(45) Date of Patent: Dec. 7, 2010

(54) 1-BENZOYL SUBSTITUTED DIAZEPINE DERIVATIVES AS SELECTIVE HISTAMINE H3 RECEPTOR AGONISTS

(75) Inventors: Gordon Bruton, Harlow (GB); Anthony Huxley, Harlow (GB); Barry Sidney Orlek, Harlow (GB); Kishore Kalidas Rana, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 909 days.

(21) Appl. No.: 10/576,492

(22) PCT Filed: Oct. 14, 2004

(86) PCT No.: PCT/EP2004/011619

§ 371 (c)(1),
(2), (4) Date: Feb. 6, 2007

(87) PCT Pub. No.: WO2005/040144

PCT Pub. Date: May 6, 2005

(65) Prior Publication Data

US 2008/0045505 A1    Feb. 21, 2008

(30) Foreign Application Priority Data

Oct. 15, 2003  (GB) ................. 0324159.3

(51) Int. Cl.
*A61P 25/00* (2006.01)
*A61K 31/551* (2006.01)
*C07D 241/12* (2006.01)
*C07D 231/14* (2006.01)
*C07D 239/26* (2006.01)
*C07D 237/08* (2006.01)
*C07D 213/81* (2006.01)
*C07D 263/32* (2006.01)
*C07D 257/04* (2006.01)
*C07D 295/18* (2006.01)

(52) U.S. Cl. ...................... 514/218; 540/575
(58) Field of Classification Search ................ 514/218; 540/575

See application file for complete search history.

(56) References Cited

U.S. PATENT DOCUMENTS 7,148,215 B2 * 12/2006 Ratcliffe et al. ............. 514/221
7,449,464 B2 * 11/2008 Martin et al. ............... 514/248

FOREIGN PATENT DOCUMENTS

WO    WO 02/12190    2/2002

* cited by examiner

*Primary Examiner*—Brenda L Coleman
(74) *Attorney, Agent, or Firm*—Bonnie L. Deppenbrock

(57) ABSTRACT

The present invention relates to novel diazepanyl derivatives of formula (I) having pharmacological activity, processes for their preparation, to compositions containing them and to their use in the treatment of neurological and psychiatric disorders.

4 Claims, No Drawings

1-BENZOYL SUBSTITUTED DIAZEPINE DERIVATIVES AS SELECTIVE HISTAMINE H3 RECEPTOR AGONISTS

CROSS-REFERENCE TO RELATED APPLICATIONS

This application is filed pursuant to 35 USC §371 as a United States National Phase Application of International Patent Application Serial No. PCT/EP2004/011619 filed on Oct. 14, 2004, which claims priority from 0324159.3 filed on Oct. 15, 2003 in the United Kingdom.

FIELD OF THE INVENTION

The present invention relates to novel diazepanyl derivatives having pharmacological activity, processes for their preparation, to compositions containing them and to their use in the treatment of neurological and psychiatric disorders.

BACKGROUND OF THE INVENTION

WO 03/00480 (Novo Nordisk A/S and Boehringer Ingleheim International GMBH) describes a series of substituted piperazines and diazepanes as H3 antagonists. WO 02/08221 (Neurogen Corporation) describes a series of substituted piperazines and diazepanes as capsaicin receptor antagonists which are claimed to be useful in the treatment of neuropathic pain. WO 98/37077 and WO 99/42107 (Zymogenetics Inc) both describe a series of substituted heterocyclic derivatives which are claimed to act as calcitonin mimics to enhance bone formation.

The histamine H3 receptor is predominantly expressed in the mammalian central nervous system (CNS), with minimal expression in peripheral tissues except on some sympathetic nerves (Leurs et al., (1998), Trends Pharmacol. Sci. 19, 177-183). Activation of H3 receptors by selective agonists or histamine results in the inhibition of neurotransmitter release from a variety of different nerve populations, including histaminergic and cholinergic neurons (Schlicker et al., (1994), Fundam. Clin. Pharmacol. 8, 128-137). Additionally, in vitro and in vivo studies have shown that H3 antagonists can facilitate neurotransmitter release in brain areas such as the cerebral cortex and hippocampus, relevant to cognition (Onodera et al., (1998), In: The Histamine H3 receptor, ed Leurs and Timmerman, pp 255-267, Elsevier Science B.V.). Moreover, a number of reports in the literature have demonstrated the cognitive enhancing properties of H3 antagonists (e.g. thioperamide, clobenpropit, ciproxifan and GT-2331) in rodent models including the five choice task, object recognition, elevated plus maze, acquisition of novel task and passive avoidance (Giovanni et al., (1999), Behav. Brain Res. 104, 147-155). These data suggest that novel H3 antagonists and/or inverse agonists such as the current series could be useful for the treatment of cognitive impairments in neurological diseases such as Alzheimer's disease and related neurodegenerative disorders.

SUMMARY OF THE INVENTION

The present invention provides, in a first aspect, a compound of formula (I) or a pharmaceutically acceptable salt thereof:

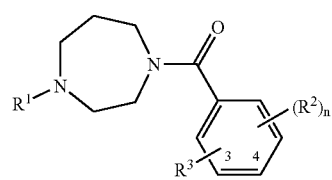

wherein:
$R^1$ represents branched $C_{3-6}$ alkyl, $C_{3-5}$ cycloalkyl or —$C_{1-4}$ alkyl $C_{3-4}$ cycloalkyl;
$R^2$ represents halogen, $C_{1-6}$ alkyl, $C_{1-6}$ alkoxy, cyano, amino or trifluoromethyl;
n represents 0, 1 or 2;
$R^3$ represents -X-aryl, -X-heteroaryl, -X-heterocyclyl, -X-aryl-aryl, -X-aryl-heteroaryl, -X-aryl-heterocyclyl, -X-heteroaryl-aryl, -X-heteroaryl-heteroaryl, -X-heteroaryl-heterocyclyl, -X-heterocyclyl-aryl, -X-heterocyclyl-heteroaryl or -X-heterocyclyl-heterocyclyl;
such that when $R^3$ represents -X-piperidinyl, -X-piperidinyl-aryl, -X-piperidinyl-heteroaryl or -X-piperidinyl-heterocyclyl said piperidinyl group is attached to X via a nitrogen atom;
wherein $R^3$ is attached to the phenyl group of formula (I) at the 3 or 4 position;
X represents a bond, O, CO, $SO_2$, $CH_2O$, $OCH_2$, $NR^4$, $NR^4CO$ or $C_{1-6}$ alkyl;
$R^4$ represents hydrogen or $C_{1-6}$ alkyl;
wherein said aryl, heteroaryl or heterocyclyl groups of $R^3$ may be optionally substituted by one or more (e.g. 1, 2 or 3) halogen, hydroxy, cyano, nitro, oxo, halo$C_{1-6}$ alkyl, halo$C_{1-6}$ alkoxy, $C_{1-6}$ alkyl, $C_{1-6}$ alkoxy, aryl$C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{3-7}$ cycloalkylcarbonyl, —$COC_{1-6}$ alkyl, $C_{1-6}$ alkoxycarbonyl, aryl$C_{1-6}$ alkyl, heteroaryl$C_{1-4}$ alkyl, heterocyclyl$C_{1-6}$ alkyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, arylsulfonyl, arylsulfonyloxy, arylsulfonyl$C_{1-6}$ alkyl, aryloxy, —CO-aryl, —CO-heterocyclyl, —CO-heteroaryl, $C_{1-6}$ alkylsulfonamido$C_{1-6}$ alkyl, $C_{1-6}$ alkylamido$C_{1-6}$ alkyl, arylsulfonamido, arylaminosulfonyl, arylsulfonamido$C_{1-6}$ alkyl, arylcarboxamido$C_{1-6}$ alkyl, aroyl$C_{1-6}$ alkyl, aryl$C_{1-6}$ alkanoyl, or a group $NR^{15}R^{16}$, —$NR^{15}$CO-aryl, —$NR^{15}$CO-heterocyclyl, —$NR^{15}$CO-heteroaryl, —$CONR^{15}R^{16}$, —$NR^{15}COR^{16}$, —$NR^{15}SO_2R^{16}$ or —$SO_2NR^{15}R^{16}$ groups, wherein $R^{15}$ and $R^{16}$ independently represent hydrogen or $C_{1-6}$ alkyl;
or solvates thereof.

In one particular aspect of the present invention, there is provided a compound of formula (I) as defined above wherein X represents a bond, O, CO, $SO_2$, $CH_2O$, $OCH_2$ or $C_{1-6}$ alkyl.

DETAILED DESCRIPTION

The term '$C_{1-6}$ alkyl' as used herein as a group or a part of the group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like.

The term '$C_{1-6}$ alkoxy' as used herein refers to an —O—$C_{1-6}$ alkyl group wherein $C_{1-6}$ alkyl is as defined herein. Examples of such groups include methoxy, ethoxy, propoxy, butoxy, pentoxy or hexoxy and the like.

The term 'C$_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term 'halogen' as used herein refers to a fluorine, chlorine, bromine or iodine atom.

The term 'haloC$_{1-6}$ alkyl' as used herein refers to a C$_{1-6}$ alkyl group as defined herein wherein at least one hydrogen atom is replaced with halogen. Examples of such groups include fluoroethyl, trifluoromethyl or trifluoroethyl and the like.

The term 'halo C$_{1-6}$ alkoxy' as used herein refers to a C$_{1-6}$ alkoxy group as herein defined wherein at least one hydrogen atom is replaced with halogen. Examples of such groups include difluoromethoxy or trifluoromethoxy and the like.

The term 'aryl' as used herein refers to a C$_{6-12}$ monocyclic or bicyclic hydrocarbon ring wherein at least one ring is aromatic. Examples of such groups include phenyl, naphthyl or tetrahydronaphthalenyl and the like.

The term 'aryloxy' as used herein refers to an —O-aryl group wherein aryl is as defined herein. Examples of such groups include phenoxy and the like.

The term 'heteroaryl' as used herein refers to a 5-6 membered monocyclic aromatic or a fused 8-10 membered bicyclic aromatic ring containing 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such fused aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and the like.

The term 'heterocyclyl' refers to a 4-7 membered monocyclic ring or a fused 8-12 membered bicyclic ring which may be saturated or partially unsaturated containing 1 to 4 heteroatoms selected from oxygen, nitrogen or sulphur. Examples of such monocyclic rings include pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridinyl, tetrahydropyrimidinyl, tetrahydrothiophenyl, tetrahydrothiopyranyl, diazepanyl, azepanyl and the like. Examples of such bicyclic rings include indolinyl, isoindolinyl, benzopyranyl, quinuclidinyl, 2,3,4,5-tetrahydro-1H-3-benzazepine, tetrahydroisoquinolinyl and the like.

Preferably, R$^1$ represents branched C$_{3-6}$ alkyl (e.g. isopropyl) or C$_{3-5}$ cycloalkyl (e.g. cyclopropyl or cyclobutyl), more preferably cyclobutyl.

Preferably, n represents 0.

Preferably, R$^3$ represents

-X-aryl (e.g. -phenyl, —CO-phenyl, —O-phenyl, —OCH$_2$-phenyl or —CH$_2$O-phenyl) optionally substituted by one or more halogen (e.g. fluorine), cyano, —COC$_{1-6}$ alkyl (e.g. —COMe) or —CONR$^{15}$R$^{16}$ (e.g. —CONH$_2$) groups;

-X-heteroaryl (e.g. -tetrazolyl, -pyrazolyl, -pyrrolyl, -oxazolyl, -isoxazolyl, -oxadiazolyl, -pyridyl, —OCH$_2$-pyridyl, —NHCO-pyridyl, -pyrimidinyl, —N(Me)-pyrimidinyl, -pyridazinyl or —OCH$_2$-pyrazinyl) optionally substituted by one or more haloC$_{1-6}$ alkyl (e.g. —CF$_3$), cyano, oxo, C$_{1-6}$ alkyl (e.g. methyl or ethyl) or —CONR$^{15}$R$^{16}$ (e.g. —CONHMe or —CON(Me)$_2$) groups;

-X-heteroaryl-aryl (e.g. -thiazolyl-phenyl) optionally substituted by one or more halogen (e.g. fluorine) atoms;

-X-aryl-heteroaryl (e.g. -phenyl-oxazolyl or -phenyl-oxadiazolyl) optionally substituted by one or more C$_{1-6}$ alkyl (e.g. methyl) groups; or -X-heterocyclyl (e.g. -thiomorpholinyl, -morpholinyl, -pyrrolidinyl or —O-tetrahydro-2H-pyran4-yl) optionally substituted by one or more oxo groups.

More preferably, R$^3$ represents

-X-aryl (e.g. -phenyl or —CO-phenyl) optionally substituted by one or more halogen (e.g. fluorine), cyano or —COC,- alkyl (e.g. —COMe) groups;

-X-heteroaryl (e.g. -oxazolyl, -isoxazolyl, -oxadiazolyl, -pyridyl, -pyrimidinyl or -pyridazinyl) optionally substituted by one or more haloC$_{1-6}$ alkyl (e.g. —CF$_3$), cyano, C$_{1-6}$ alkyl (e.g. methyl) or —CONR$^{15}$R$^{16}$ (e.g. —CONHMe) groups;

-X-heteroaryl-aryl (e.g. -thiazolyl-phenyl) optionally substituted by one or more halogen (e.g. fluorine) atoms; or -X-heterocyclyl (e.g. -morpholinyl).

Most preferably, R$^3$ represents

-X-aryl (e.g. -phenyl) optionally substituted by one or more cyano or —COC$_{1-6}$ alkyl (e.g. —COMe) groups; or -X-heteroaryl (e.g. -pyridyl) optionally substituted by one or more haloC$_{1-6}$ alkyl (e.g. —CF$_3$) or cyano groups.

Especially preferably, R$^3$ represents -pyridyl optionally substituted by one or more haloC$_{1-6}$ alkyl (e.g. —CF$_3$) or cyano groups.

Preferably, R$^3$ is attached to the phenyl group of formula (I) at the 4 position.

Preferably, X represents a bond, CO, O, NR$^4$, NR$^4$CO, CH$_2$O or OCH$_2$ more preferably a bond.

Preferably, R$^4$ represents hydrogen or methyl.

Preferably, R$^3$ is attached to the phenyl group of formula (I) at the 4 position.

Preferred compounds according to the invention include examples E1-E58 as shown below, or a pharmaceutically acceptable salt thereof.

Compounds of formula (I) may form acid addition salts with acids, such as conventional pharmaceutically acceptable acids, for example maleic, hydrochloric, hydrobromic, phosphoric, acetic, fumaric, salicylic, sulphate, citric, lactic, mandelic, tartaric and methanesulphonic. Salts, solvates and hydrates of histamine H3 receptor antagonists or inverse agonists therefore form an aspect of the invention.

Certain compounds of formula (I) are capable of existing in stereoisomeric forms. It will be understood that the invention encompasses all geometric and optical isomers of these compounds and the mixtures thereof including racemates. Tautomers also form an aspect of the invention.

The present invention also provides a process for the preparation of a compound of formula (I) or a pharmaceutically acceptable salt thereof, which process comprises:

(a) reacting a compound of formula (II)

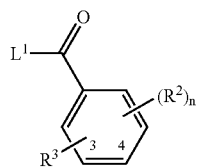

wherein $R^2$, n and $R^3$ are as defined above and $L^1$ represents OH or a suitable leaving group, such as a halogen atom (e.g. chlorine), with a compound of formula (III)

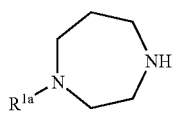

wherein $R^{1a}$ is as defined above for $R^1$ or is a group convertible to $R^1$; or (b) reacting a compound of formula (IV)

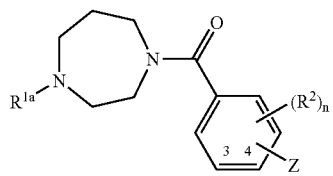

with a compound of formula $R^3$-$L^2$, wherein $R^{1a}$, $R^2$, $R^3$ and n are as defined above, $L^2$ represents a suitable leaving group such as a halogen atom and Z represents a boronic acid ester group attached at the 3 or 4 position of the phenyl ring, such as a pinacol ester e.g. a group of formula $Z^a$:

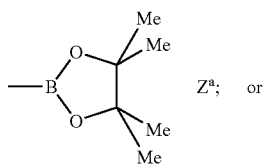

(c) deprotecting a compound of formula (I) which is protected; and optionally thereafter
(d) interconversion to other compounds of formula (I).

Process (a) typically comprises activation of the compound of formula (II) wherein $L^1$ represents OH with a coupling reagent such as 1-(3-dimethylaminopropyl)-3-ethylcarbodiimide hydrochloride (EDC) in the presence of 1-hydroxybenzotriazole (HOBT) in a suitable solvent such as dichloromethane followed by reaction with the compound of formula (III).

Process (a) may also involve halogenation of the compound of formula (II) wherein $L^1$ represents OH with a suitable halogenating agent (e.g. thionyl chloride or oxalyl chloride) followed by reaction with the compound of formula (III) in the presence of a suitable base such as triethylamine or a solid supported base such as diethylaminomethylpolystyrene in a suitable solvent such as dichloromethane.

Process (b) typically comprises the use of a catalyst such as tetrakis(triphenylphosphine)palladium(0) in a solvent such as acetonitrile with a base e.g. sodium carbonate.

In process (c), examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2',2',2'-trichloroethoxycarbonylv benzyloxycarbonyl or t-butoxycarbonyl) and arylalkyl (e.g. benzyl), which may be removed by hydrolysis (e.g. using an acid such as hydrochloric acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (d) may be performed using conventional interconversion procedures such as epimerisation, oxidation, reduction, alkylation, nucleophilic or electrophilic aromatic substitution, ester hydrolysis or amide bond formation.

Compounds of formula (II) and (III) are either known in the literature or can be prepared by analogous methods.

Compounds of formula (IV) may be prepared by reacting a compound of formula (V)

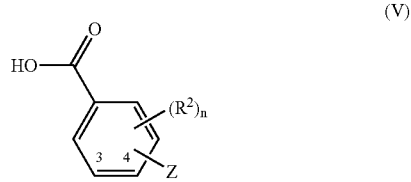

wherein $R^2$, n and Z are as defined above, with a compound of formula (III) as defined above. This process typically comprises activation of the compound of formula (V) with a coupling reagent such as 1-(3-dimethylaminopropyl)-3-ethylcarbodiimide hydrochloride (EDC) in the presence of 1-hydroxybenzotriazole (HOBT) in a suitable solvent such as DMF.

Compounds of formula (V) are either known in the literature or can be prepared by analogous methods.

Compounds of formula (I) and their pharmaceutically acceptable salts have affinity for and are antagonists and/or inverse agonists of the histamine H3 receptor and are believed to be of potential use in the treatment of neurological diseases including Alzheimer's disease, dementia (including Lewy body dementia and vascular dementia), age-related memory dysfunction, mild cognitive impairment, cognitive deficit, epilepsy, neuropathic pain, inflammatory pain, migraine, Parkinson's disease, multiple sclerosis, stroke and sleep disorders (including narcolepsy and sleep deficits associated with Parkinson's disease); psychiatric disorders including schizophrenia (particularly cognitive deficit of schizophrenia), attention deficit hyperactivity disorder, depression, anxiety and addiction; and other diseases including obesity and gastro-intestinal disorders.

It will be appreciated that certain compounds of formula (I) believed to be of potential use in the treatment of Alzheimer's disease and cognitive deficit of schizophrenia will advantageously be CNS penetrant, e.g. have the potential to cross the blood-brain barrier.

It will also be appreciated that compounds of formula (I) are expected to be selective for the histamine H3 receptor over other histamine receptor subtypes, such as the histamine H1 receptor. Generally, compounds of the invention may be at least 10 fold selective for H3 over H1, such as at least 100 fold selective.

Thus the invention also provides a compound of formula (I) or a pharmaceutically acceptable salt thereof, for use as a therapeutic substance in the treatment or prophylaxis of the above disorders, in particular cognitive impairments in diseases such as Alzheimer's disease and related neurodegenerative disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a pharmaceutically acceptable salt thereof and a pharmaceutically acceptable carrier.

The present invention further provides a pharmaceutical composition which comprises the compound of formula (I) or a pharmaceutically acceptable salt thereof and a pharmaceutically acceptable carrier.

Compounds of formula (I) may be used in combination with other therapeutic agents, for example medicaments claimed to be useful as either disease modifying or symptomatic treatments of Alzheimer's disease. Suitable examples of such other therapeutic agents may be agents known to modify cholinergic transmission such as 5-HT$_6$ antagonists, M1 muscarinic agonists, M2 muscarinic antagonists or acetylcholinesterase inhibitors. When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Descriptions and Examples illustrate the preparation of compounds of the invention.

It will be appreciated that hydrochloride salt compounds may be converted into the corresponding free base compounds by treatment with saturated aqueous potassium carbonate solution followed by extraction into a suitable solvent such as diethyl ether or DCM.

Description 1 (Method A)

1-tert-Butyl-4-(isopropyl)-hexahydro-1H-1,4-diazepine-1-carboxylate (D1)

tert-Butyl-hexahydro-1H-1,4-diazepine-1-carboxylate (10.0 g) was dissolved in DCM (200 ml). Acetone (7.33 ml) was added and the reaction was left to stir for 5 min. Sodium triacetoxyborohydride (21.0 g) was then added and the reaction was stirred at rt for 16 h. The reaction mixture was washed with saturated potassium carbonate solution (2×200 ml). The organic layer was dried (magnesium sulphate) and evaporated to give the title compound (D1) as a clear oil (11.0 g).

Description 1 (Method B)

1-tert-Butyl-4-(isopropyl)-hexahydro-1H-1,4-diazepine-1-carboxylate (D1)

tert-Butyl-hexahydro-1H-1,4-diazepine-1-carboxylate (25.06 g) was dissolved in acetonitrile (250 ml). Anhydrous potassium carbonate (34.5 g) and 2-iodopropane (63 g, 37 ml) were added and the mixture was heated at reflux for 18 h. The cooled mixture was filtered and the solids were washed with acetonitrile. The combined filtrates were evaporated and the residual oil was dissolved in diethyl ether, washed with water, sodium thiosulphate solution and brine, dried ($Na_2SO_4$) and evaporated to give the title compound (D1) as a light brown oil (29.8 g).

Description 2

1-(Isopropyl)-hexahydro-1H-1,4-diazepine dihydrochloride (D2)

1-tert-Butyl-4-(isopropyl)-hexahydro-1H-1,4-diazepine-1-carboxylate (D1) (11.0 g) was dissolved in methanol (200 ml) and 4N HCl in dioxan (100 ml) was added. The reaction was stirred at rt for 2 h and then evaporated to give the title compound (D2) as a white solid (9.6 g). $^1$H NMR δ ($CDCl_3$): 11.35 (1H, s), 10.22 (1H, s), 9.72 (1H, s), 4.15-3.52 (9H, m), 2.83-2.40 (2H, m), 1.47 (6H, d, J=6.24 Hz).

Description 3

1-tert-Butyl-4-(cyclobutyl)-hexahydro-1-H1,4-diazepine-1-carboxylate (D3)

tert-Butyl-hexahydro-1H-1,4-diazepine-1-carboxylate (10.0 g) was dissolved in DCM (300 ml). Cyclobutanone (7.5 ml) was added and the reaction was left to stir for 5 min. Sodium triacetoxyborohydride (21.1 g) was then added and the reaction was stirred at rt for 16 h. The reaction mixture was washed with saturated potassium carbonate solution (2×200 ml). The organic layer was dried (magnesium sulphate) and evaporated to give the title compound (D3) as a clear oil (11.3 g).

Description 4

1-(Cyclobutyl)hexahydro-1H-1,4-diazepine dihydrochloride (D4)

1-tert-Butyl4-(cyclobutyl)-hexahydro-1-H-1,4-diazepine-1-carboxylate (D3) (11.3 g) was dissolved in methanol (200 ml) and 4N HCl in dioxan (100 ml) was added. The reaction was stirred at rt for 3 h and then co-evaporated from toluene (3×50 ml) to give the title compound (D4) as a white solid (9.8 g). $^1$H NMR δ (DMSO-d6): 11.95 (1H, s), 9.55 (1H, s), 9.64 (1H, s), 3.78-3.08 (9H, m), 2.51-2.07 (6H, m), 1.80-1.51 (2H, m).

Description 5

Ethyl 4-(tetrahydro-2H-pyran-4-yloxy)benzoate (D5)

An ice-cold solution of ethyl 4-hydroxybenzoate (0.82 g), 4-hydroxy-tetrahydro-2H-pyran (0.5 g) and triphenylphosphine in THF (50 ml) was treated dropwise with diisopropyl azodicarboxylate (1.69 ml). After 15 min the cooling bath was removed and the reaction stood overnight at rt. The mixture was evaporated, redissolved in toluene and successively washed with 2N sodium hydroxide (2×20 ml), water (2×20 ml) and brine (20 ml). After drying (magnesium sulfate) the solution was loaded directly on to a silica flash column (step gradient 10-30% EtOAc in light petroleum 40-60) to give the title compound (D5) (0.75 g). $^1$H NMR δ ($CDCl_3$): 7.98 (2H, d, J=8.5Hz), 6.91 (2H, d, J=8.5 Hz), 4.60 (1H, m), 4.35 (2H, q, J=9.8 Hz), 3.98 (2H, m), 3.57 (2H, m), 2.05 (2H, m), 1.80 (2H, m), 1.38 (3H, t, J=9.8 Hz).

Description 6

4-(Tetrahydro-2H-pyran-4-yloxy)benzoic acid (D6)

A solution of ethyl 4-(tetrahydro-2H-pyran-4-yloxy)benzoate (D5) (0.73 g) in EtOH (10 ml) was treated with 1 M NaOH (5.84 ml) and the mixture stirred at 60° C. for 5 h. The solution was cooled to rt and the EtOH was evaporated. The aqueous was washed with DCM (2×10 ml) and acidified. The solid was filtered off, washed with water and dried to give the title compound (D6) (0.55 g). MS electrospray (-ion) 221 (M-H). $^1$H NMR δ (DMSO-d6): 7.87 (2H, d, J=8.5 Hz), 7.05 (2H, d, J=8.5 Hz), 4.69 (1H, m), 3.85 (2H, m), 3.50 (2H, m), 1.98 (2H, m), 1.59 (2H, m).

Description 7

1-Cyclobutyl-4-{[4-(4,4,5,5-tetramethyl-1,3,2-dioxaborolan-2-yl)phenyl]carbonyl}hexahydro-1-H1,4-diazepine (D7)

4-(4,4,5,5-Tetramethyl-1,3,2-dioxaborolan-2-yl)benzoic acid (1.24 g) in dry DMF (30 ml) was treated with EDC (1.48 g) and HOBT (0.67 g). The reaction mixture was stirred at rt for 5 min, followed by the addition of 1-(cyclobutyl)hexahydro-1H-1,4-diazepine dihydrochloride (D4) (1.13 g) and triethylamine (2.7 ml). The mixture was stirred at rt overnight. The reaction mixture was then poured into water (250 ml) and extracted with EtOAc (2×35 ml). The combined organic layers were washed with saturated aqueous sodium hydrogen carbonate (2×30 ml) followed by water (5×30 ml). After drying (magnesium sulphate) the solution was evaporated to give the title compound (D7) as an oil (0.84 g).MS electrospray (+ve ion) 385 ($MH^+$).

Description 8

Methyl 4-(6-cyano-3-pyridinyl)benzoate (D8)

4-Methoxycarbonylphenyl boronic acid (0.5 g) and 5-bromo-2-pyridinecarbonitrile (0.5 g) in a mixture of THF (5 ml) and water (5 ml) were treated with tetrakis(triphenyl phosphine)palladium(0) (0.32 g) and potassium carbonate (1 g). A further amount of THF (5 ml) was added and the reaction was heated at 80° C. for 1 h. After cooling the reaction mixture was diluted with EtOAc (30 ml) and washed with saturated aqueous sodium hydrogen carbonate solution. The organic layer was dried (magnesium sulfate) and concentrated to give a crude residue that was purified by column chromatography (silica-gel, gradient 0-100% EtOAc in hexane) to give the title compound (D8) as a white solid (0.5 g). LCMS electrospray (+ve) 239 ($MH^+$).

Description 9

4-(6-Cyano-3-pyridinyl)benzoic acid (D9)

Methyl 4-(6-cyano-3-pyridinyl)benzoate (D8) (0.5 g) in dioxane (30 ml) was treated with 1.1 eq aqueous LiOH solution (2.3 ml), 1N) and stirred at rt for 2 days. Solvent was removed by evaporation to give a white solid which was dissolved in water (10 ml) and acidified with 2N HCl to give a white solid which was filtered and dried to give the title compound (D9) (0.35 g). LCMS electrospray (+ve) 224 (MH$^+$).

Description 10

5-Bromo-2-pyridinecarboxylic acid (D10)

4-Bromobenzonitrile (4.45 g) was heated at reflux in concentrated hydrochloric acid (60 ml) for 3 h. After cooling, white crystals were filtered off and dried in a vacuum oven to give the title compound (D10) (3.46 g). LCMS electrospray (+ve) 203 (MH$^+$).

Description 11

5-Bromo-N-methyl-2-pyridinecarboxamide (D11)

5-Bromo-2-pyridinecarboxylic acid (D10) (1 g) was dissolved in dry DMF (50 ml) and treated with methylamine hydrochloride (0.42 g), EDC (1.29), HOBT (0.56 g) and Et$_3$N (2.4 ml). The reaction was stirred at rt overnight then poured into water (200 ml) and extracted with DCM (50 ml). The organic extract was washed with brine (5×50 ml), dried (magnesium sulfate) and evaporated to give the title compound (D11) as a yellow crystalline solid (0.45 g). LCMS electrospray (+ve) 349 (MH$^+$).

Description 12

1-(Isopropyl)-4-{[4-(4,4,5,5-tetramethyl-1,3,2-dioxaborolan-2-yl)phenyl]carbonyl}hexahydro-1H-1,4-diazepine (D12)

The tile compound (D12) was prepared in a similar manner to Description 7 from 1-(isopropyl)-hexahydro-1H-1,4-diazepine (free base of D2) and 4-(4,4,5,5-tetramethyl-1,3,2-dioxaborolan-2-yl)benzoic acid and isolated as a brown oil. LCMS electrospray (+ve) 373 (MH$^+$).

Description 13

5-Bromo-2-trifluoromethylpyrimidine (D13)

A mixture of potassium fluoride (1.77 g) and cuprous iodide (5.79 g) was stirred and heated together using a heat gun under vacuum (~1 mm) for 20 min. After cooling, dimethyl formamide (20 ml) and N-methyl pyrrolidinone (20 ml) were added followed by (trifluoromethyl)trimethylsilane (4.1 ml) and 5-bromo-2-iodopyrimidine (6.5 g). The mixture was stirred at rt for 5 h and then the brown solution was poured into 6N ammonia solution. The product was extracted into ethyl acetate and the extracts were washed with sodium bicarbonate solution and brine and then dried (Na$_2$SO$_4$) and evaporated. Chromatography on silica gel (elution with 20-50% dichloromethane in pentane) gave the title compound (D13) as a white solid (2.4 g). $^1$H NMR (CDCl$_3$): 8.97 (2H, s).

Description 14

4-(4-Bromophenyl)-2-methyl-oxazole (D14)

4-Bromophenacyl bromide (21.3 g) and acetamide (11.3 g) were heated together at 130° C. under argon. After 2.5 h the reaction mixture was allowed to cool, and partitioned between water (150 ml) and Et$_2$O (150 ml). The organic phase was washed with aqueous NaOH (0.5N), aqueous HCl (0.5M) and saturated aqueous NaCl solution (100 ml) of each), dried (MgSO$_4$) and evaporated to give a brown solid which was recrystallised from hexanes to give the title compound (D14) as an orange solid (4.1 g). LCMS electrospray (+ve) 239 (MH$^+$).

Description 15

5 5-(4-Bromophenyl)-2-methyl-oxazole (D15)

Trifluoromethanesulfonic acid (6.6 ml) was added to a flask containing iodobenzene diacetate (12.2 g) and MeCN (200 ml) at rt. After 25 min. a solution of 4'-bromoacetophenone (5 g) in MeCN (50 ml) was added and the resultant mixture heated at reflux for 6 h. The reaction was allowed to cool to rt before the solvent was evaporated and the residue partitioned between saturated aqueous Na$_2$CO$_3$ (150 ml) and EtOAc (150 ml). The organic phase was washed with saturated brine (150 ml), dried (MgSO$_4$) and evaporated to give an orange solid. The crude product was purified by column chromatography (silica gel, 50% EtOAc in hexane) to give the title compound (D15) as a pale yellow solid (3.5 g). LCMS electrospray (+ve) 239 (MH$^+$).

Description 16

3-(4-Bromophenyl)-5-methyl-1,2,4-oxadiazole (D16)

Step 1:
4-Bromo-N-hydroxy-benzenecarboximidamide

4-Bromophenylcarbonitrile (10.2 g), hydroxylamine hydrochloride (7.8 g) and Et$_3$N (11.3 g) were dissolved in EtOH (250 ml) and the reaction mixture was heated at reflux for 3 h, after which it was evaporated to form a white precipitate of the desired amidoxime, which was filtered off and washed with water (25 ml). The filtrate was extracted into EtOAc (2×25 ml), and the combined organic extracts were dried (Na$_2$SO$_4$) and evaporated to give a second crop of the subtitle compound (combined yield=11.1 g). LCMS electrospray (+ve) 216 (MH$^+$).

Step 2: 3-(4-Bromophenyl)-5-methyl-1,2,4-oxadiazole

The product from D16, step 1 was suspended in acetic anhydride and heated to 100° C. for 4 h, then 120° C. for 3 h. After cooling the reaction mixture was evaporated to give a brown solid. This was partitioned between saturated aqueous NaHCO$_3$ and EtOAc. The organic phase was washed with saturated aqueous NaCl, dried (Na$_2$SO$_4$) and evaporated to give a yellow solid. The crude product was purified by column chromatography (silica gel, 10-100% gradient of EtOAc in hexane) to give the title compound (D16) as a white solid (6.2 g). LCMS electrospray (+ve) 240 (MH$^+$).

Description 17

2-(4-Bromophenyl)-oxazole (D17)

Step 1: 4-Bromo-N-(2,2-dimethoxyethyl)-benzamide

Potassium carbonate (8.0 g) was added to a solution of 2,2-dimethoxyethylamine in water (90 ml) and acetone (40 ml) at rt. The reaction mixture was cooled in an ice-water bath and 4-bromobenzoyl chloride (16.4 g) dissolved in acetone (70 ml) was added drop-wise over 90 min. The stirred reaction mixture was allowed to warm to rt. After a further 2 h the reaction mixture was extracted into EtOAc (3×75 ml), the combined organics were washed with saturated aqueous sodium hydrogen carbonate, dried (MgSO$_4$) and evaporated to give the amide as an off white solid (18.5 g). LCMS electrospray (+ve) 289 (MH$^+$).

Step 2: 2-(4-Bromophenyl)-oxazole

The product of D17, step 1 was suspended in Eaton's reagent (200 ml), the reaction mixture was purged with argon and heated to 240° C. for 9 h. The reaction mixture was then allowed to cool and stirred for 65 h at rt. The crude mixture was poured over ice (1 L) and stirred for 1 h. The aqueous mixture was extracted into EtOAc (2×250 ml), dried (MgSO$_4$) and evaporated to give a grey powder. This crude solid was dissolved in THF (300 ml) and EtOH (300 ml), and Hunig's base (21.1 ml) was added. MP-carbonate resin (40.1 g) and PS-thiophenol resin (69.7 g) were suspended in the reaction mixture, which was stirred for 24 h. The suspension was filtered and the solid phase resins washed with 1:1 THF: EtOH (3×600 ml), and the combined organics evaporated to give the title compound (D17) as a white solid (9.0 g). LCMS electrospray (+ve) 225 (MH$^+$).

Description 18

4-(3-Methyl-1,2,4-oxadiazol-5-yl)benzoic acid (D18)

Methyl 4-(3-methyl-1,2,4-oxadiazol-5-yl)benzoate (J. R. Young and R. J. DeVita, Tetrahedron Lett., 1998, 39, 3931) was dissolved in a mixture of dioxan (110 ml), water (70 ml) and isopropanol (30 ml), and lithium hydroxide (1.38 g) was added. The mixture was stirred at room temperature for ca 5 h and then the mixture was acidified to ca pH 4 by addition of Amberlyst 15 H$^+$ resin. The resin was removed by filtration and the filtrate was concentrated in vacuo. The solid white precipitate which was obtained was collected by filtration, washed with water on the filter and dried in vacuo at 40° C. for 48 h to give the title compound (D18) (4.23 g).

EXAMPLE 1

4'-[(4-Cyclobutylhexahydro-1H-1,4-diazepin-1-yl)carbonyl]-4-biphenylcarbonitrile hydrochloride (E1)

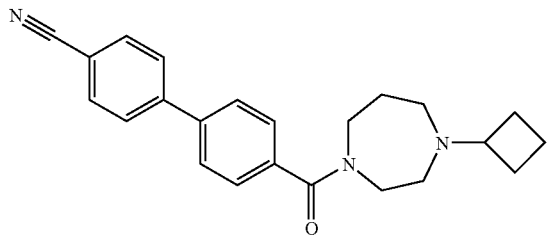

1-(Cyclobutyl)-hexahydro-1H-1,4-diazepine dihydrochloride (D4) (0.15 g) was stirred with diethylaminomethyl polystyrene (1.0 g), HOBT (0.045 g), 4'-cyano-4-biophenylcarboxylic acid (0.16 g) in DCM (5 ml). EDC (0.16 g) was then added and the reaction was stirred at rt for 16 h. The polymer supported base was filtered off and the filtrate was diluted with DCM (10 ml) and washed with saturated sodium hydrogen carbonate (2×15 ml). The organic layer was then loaded directly onto a silica column eluting with 0-10% MeOH (containing 10% 0.880 ammonia solution)/DCM. The isolated free base product was dissolved in DCM (5 ml) and treated with excess 1N HCl/diethyl ether solution (1 ml) and stirred for 10 min. The mixture was evaporated (co-evaporated with acetone 2×10 ml), triturated with acetone, then dried at 50° C. under high vacuum for 16 h to yield the title compound (E1) as a pale solid (0.119 g). MS electrospray (+ion) 360 (MH$^+$). $^1$H NMR δ (DMSO-d6): 10.60 (1H, s), 7.97 (4H, m), 7.86 (2H, d, J=8.4 Hz), 7.60 (2H, d, J=7.6 Hz), 4.18 (1H, m), 3.89-3.37 (6H, m), 3.10 (2H, m), 2.40-1.59 (8H, m).

EXAMPLE 2

1-{4'-[(4-Cyclobutylhexahydro-1H-1,4-diazepin-1-yl)carbonyl]-4-biphenylyl}ethanone hydrochloride (E2)

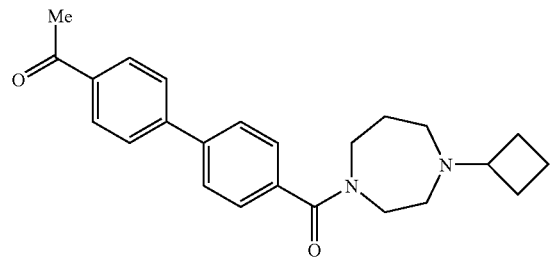

1-(Cyclobutyl)-hexahydro-1H-1,4-diazepine dihydrochloride (D4) (0.15 g) was stirred with diethylaminomethyl polystyrene (1.0 g), HOBT (0.045 g) and 4'-acetyl-4-biphenylcarboxylic acid (0.13 g) in DCM (5 ml). EDC (0.16 g) was then added and the reaction stirred at rt for 16 h. The polymer supported base was filtered off and the filtrate was diluted with DCM (10 ml) and washed with saturated sodium hydrogen carbonate (2×15 ml). The organic layer was loaded directly onto a silica column eluting with 0-10% MeOH (containing 10% 0.880 ammonia solution)/DCM. The isolated free base product was dissolved in DCM (5 ml) and treated with excess 1N HCl/diethyl ether solution (1 ml) and stirred for 10 min. The mixture was evaporated (co-evaporated with acetone 2×10 ml), triturated with acetone, then dried at 50° C. under high vacuum for 16 h to yield the title compound (E2) as a pale solid (0.055 g). MS electrospray (+ion) 377 (MH$^+$). $^1$H NMR δ (DMSO-d6): 10.57 (1H, s), 9.07 (2H, d, J=6.4 Hz), 7.88 (4H, m), 7.60 (2H, d, J=7.6 Hz), 4.15 (1H, m), 3.82-3.33 (6H, m), 3.02 (2H, m), 2.62 (3H, s), 2.41-1.62 (8H, m).

EXAMPLES 3-6

(E3-E6)

Examples 3-6 were prepared from 1-(cyclobutyl)-hexahydro-1H-1,4-diazepine dihydrochloride (D4) and the appropriate carboxylic acid, using the procedure described in Example 1 and displayed $^1$H NMR and mass spectral data that were consistent with structure.

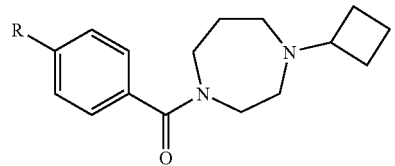

| Example No | R | Mass Spectrum (ES$^+$) |
|---|---|---|
| E3 | ![phenyl] | [MH]$^+$ 335 |

-continued

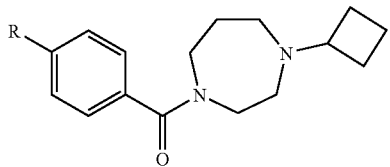

| Example No | R | Mass Spectrum (ES⁺) |
|---|---|---|
| E4 | (phenyl ketone) | [MH]⁺ 363 |
| E5 | (methoxyphenyl) | [MH]⁺ 351 |
| E6 | (methoxymethylphenyl) | [MH]⁺ 365 |

EXAMPLE 7

1-Cyclobutyl-4-{[4-tetrazol-1-yl)phenyl]carbonyl}hexahydro-1H-1,4-diazepine hydrochloride (E7)

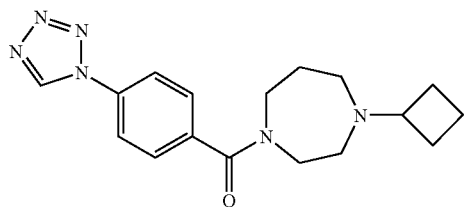

1-(Cyclobutyl)-hexahydro-1H-1,4-diazepine dihydrochloride (D4) (0.15 g) was stirred with diethylaminomethyl polystyrene (1.0 g), HOBT (0.045 g) and 4-(tetrazol-1-yl)-benzoic acid (0.14 g) in DCM (5 ml). EDC (0.165 g) was then added and the reaction was stirred at rt for 16 h. The polymer supported base was filtered off and the filtrate was diluted with DCM (10 ml) and washed with saturated sodium hydrogen carbonate (2×15 ml). The organic layer was then loaded directly onto a silica column eluting with 0-10% MeOH (containing 10% 0.880 ammonia solution)/DCM. The isolated free base product was dissolved in DCM (5 ml) and treated with excess 1N HCl/diethyl ether solution (1 ml) and stirred for 10 min. The mixture was evaporated (co-evaporated with acetone 2×10 ml), triturated with acetone, then dried at 50° C. under high vacuum for 16 h to yield the title compound (E7) as a pale solid (0.096 g). MS electrospray (+ion) 327 (MH⁺). ¹H NMR δ (DMSO-d6): 11.11 (1H, s), 10.18 (1H, s), 8.02 (2H, d, J=8.4 Hz), 7.76 (2H, d, J=8.0 Hz), 4.17 (1H, m), 3.81-3.27 (6H, m), 3.11 (2H, m), 2.47-1.95 (6H, m), 1.80-1.59 (2H, m).

EXAMPLE 8

1-Cyclobutyl-4-({4-[4-(4-fluorophenyl)-1,3-thiazol-2-yl]phenyl}carbonyl) hexahydro-1H-1,4-diazepine hydrochloride (E8)

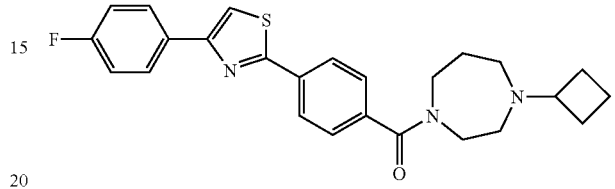

The title compound (E8) was prepared from 1-(cyclobutyl)-hexahydro-1H-1,4-diazepine dihydrochloride (D4) and 4-[4-(4-fluorophenyl)-1,3-thiazol-2-yl]benzoic acid using the procedure described in Example 7. MS APCl 436 (MH⁺).

EXAMPLE 9

1-Cyclobutyl-4-{[4-(1,1-dioxido-4-thiomorpholinyl)phenyl]carbonyl}hexahydro-1H-1,4-diazepine hydrochloride (E9)

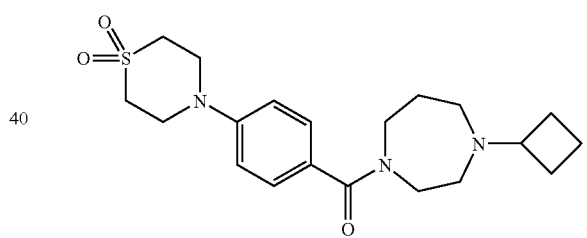

1-(Cyclobutyl)-hexahydro-1H-1,4-diazepine dihydrochloride (D4) (0.15 g) was stirred with diethylaminomethyl polystyrene (1.0 g), HOBT (0.045 g), 4-(1,1-dioxido-4-thiomorpholinyl)benzoic acid (0.186 g) in DCM (5 ml). EDC (0.165 g) was then added and the reaction was stirred at rt for 16 h. The polymer supported base was filtered off and the filtrate was diluted with DCM (10 ml) and washed with saturated sodium hydrogen carbonate (2×15 ml). The organic layer was then loaded directly onto a silica column and eluted with 0-10% MeOH (containing 10% 0.880 ammonia solution)/DCM. The isolated free base product was dissolved in DCM (5 ml) and treated with excess 1N HCl/diethyl ether solution (1 ml) and stirred for 10 min. The mixture was evaporated (co-evaporated with acetone 2×10 ml), triturated with acetone, then dried at 50° C. under high vacuum for 16 h to yield the title compound (E9) as a pale solid (0.086 g). MS electrospray (+ion) 392 (MH⁺). ¹H NMR δ (DMSO-d6): 10.5 (1H, s), 7.37 (2H, d, J=8.4 Hz), 7.07 (2H, d, J=8.8 Hz), 4.18-3.24 (10H, m), 3.11 (4H, m), 3.10-2.85 (2H, m), 2.45-1.98 (7H, m), 1.80-2.54 (2H, m).

EXAMPLE 10

1-(Isopropyl)-4-{[14-(tetrahydro-2H-pyran-4-yloxy)phenyl]carbonyl)hexahydro-1H-1,4-diazepine hydrochloride (E10)

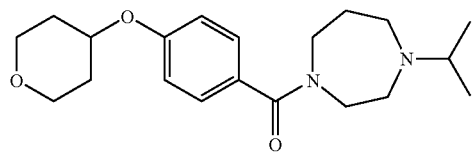

A stirred suspension of 4-(tetrahydro-2H-pyran4-yloxy)benzoic acid (D6) (222 mg) in DCM (5 ml) at rt was treated with oxalyl chloride (0.28 ml) and 10% DMF in DCM (1 drop). After 1 h the solution was evaporated and then re-evaporated from DCM (2×5 ml). The acid chloride was redissolved in DCM (10 ml) and treated with 1-(isopropyl)-hexahydro-1H-1,4-diazepine dihydrochloride (D2) (178 mg) and diethylaminomethyl polystyrene (3.2 mmol/g, 938 mg). After stirring overnight the mixture was loaded directly on to a silica gel flash column [step gradient 6-10% MeOH (containing 10% 0.880 ammonia solution) in DCM]. Fractions containing the required product were evaporated, then redissolved in DCM and treated with excess 4M HCl in dioxan. Crystallisation from acetone afforded the title compound (E10) (225 mg). MS electrospray (+ion) 347 (MH$^+$). $^1$H NMR δ (DMSO-d6): 10.45 (1H, m), 7.41 (2H, d, J=8.5 Hz), 7.02 (2H, d, J=8.5 Hz), 4.63 (2H, m), 4.02 (1H, m), 3.02-3.93 (13H, m), 2.32 (1H, m), 1.96 (2H, m), 1.61 (2H, m), 1.27 (6H, d, J=6.5 Hz).

EXAMPLE 11

1-Cyclobutyl-4-({4-[6-(trifluoromethyl)-3-pyridinyl]phenyl}carbonyl)hexahydro-1H-1,4-diazepine hydrochloride (E11)

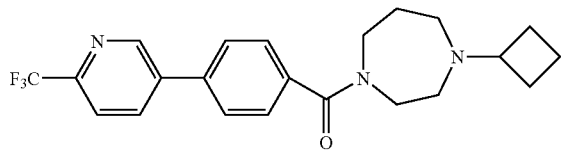

A mixture of 1-cyclobutyl-4-{[4-(4,4,5,5-tetramethyl-1,3,2-dioxaborolan-2-yl)phenyl]carbonyl}hexahydro-1H-1,4-diazepine (D7) (0.28 g) and 5-bromo-2-(trifluoromethyl)pyridine (F. Cottet and M. Schlosser, Eur. J. Org. Chem., 2002, 327) in dry and degassed acetonitrile (3.5 ml) was treated with tetrakis(triphenyl phosphine)palladium(0) (0.050 g), and 2M aqueous Na$_2$CO$_3$ solution (0.6 ml). The reaction mixture was heated at 140° C. for 5 min in an Emrys Optimiser microwave reactor. The crude reaction mixture was then diluted with MeOH (10 ml) and the solution was poured directly onto an SCX column (10 g) and washed first with MeOH (60 ml) and then eluted with 2M ammonia in MeOH solution (60 ml). The ammonia/methanol fractions were concentrated and further purified on a Waters mass directed preparative HPLC. The required fractions were concentrated and the residual gum was redissolved in MeOH (1 ml) and treated with ethereal HCl (1 ml), 1N. After evaporation of solvent the residue was triturated with diethyl ether to give the title hydrochloride salt (E11) as a white solid (0.088 g). $^1$H NMR δ (methanol-d4): 1.76-1.89 (2H, m), 2.18-2.38 (6H, m), 3.09-3.18 (2H, m), 3.47-3.9 (6H, m), 4.31-4.35 (1H, m), 7.64 (2H, d, J=8 Hz), 7.88 (1H, d, J=8 Hz), 7.92 (2H, d, J=8 Hz), 8.33 (1H, d, J=8 Hz), 9.02 (1H, s). LCMS electrospray (+ve) 404 (MH$^+$).

EXAMPLE 12

6-{4-[(4-Cyclobutylhexahydro-1H-1,4-diazepin-1-yl)carbonyl]phenyl}-3-cyanopyridine hydrochloride (E12)

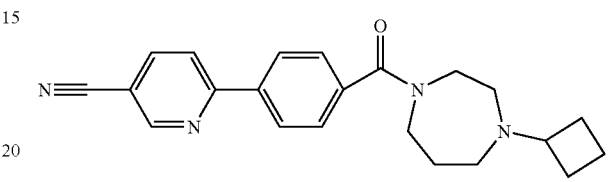

The title compound (E12) was prepared in a similar manner to Example 11 from 1-cyclobutyl-4-{[4-(4,4,5,5-tetramethyl-1,3,2-dioxaborolan-2-yl)phenyl]carbonyl}hexahydro-1H-1,4-diazepine (D7) (0.15 g) and 6-chloronicotinonitrile (0.054 g). The crude reaction mixture was purified by flash chromatography [silica gel, step gradient 0-15% MeOH (containing 10% 0.88 ammonia solution) in DCM]. The free base compound was converted into the HCl salt in dry DCM (2 ml) with ethereal HCl (1 ml), 1N. Evaporation of solvent afforded the title compound (E12) as a white solid (0.046 g). $^1$H NMR δ (methanol-d4): 1.78-1.90 (2H, m), 2.1-2.4 (6H, m), 3.03-3.2 (2H, m), 3.5-3.9 (6H, m), 4.28-4.35 (1H, m), 7.65 (2H, d, J=8 Hz), 8.13 (1H, d, J=8 Hz), 8.23-8.26 (3H, m), 8.99 (1H, d, J=2.4 Hz). LCMS electrospray (+ve) 361 (MH$^+$).

EXAMPLE 13

5-{4-[(4-Cyclobutylhexahydro-1H-1,4-diazepin-1-yl)carbonyl]phenyl}-N-methyl-2-pyridinecarboxamide hydrochloride (E13)

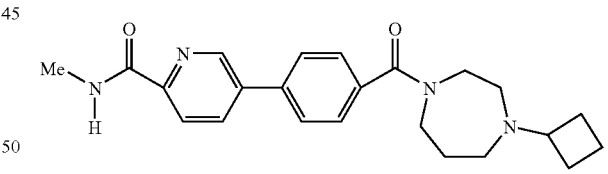

The title compound (E13) was prepared in a similar manner to Example 11 from 1-cyclobutyl-4-{[4-(4,4,5,5-tetramethyl-1,3,2-dioxaborolan-2-yl)phenyl]carbonyl}hexahydro-1H-1,4-diazepine (D7) (0.22 g) and 5-bromo-N-methyl-2-pyridinecarboxamide (D11) (0.11 g). The crude mixture after SCX work-up was purified on a Waters mass directed preparative HPLC. Pure fractions were concentrated, redissolved in dry DCM (2 ml) and treated with 1N ethereal HCl. After evaporation of solvents the title compound (E13) was obtained as a white solid (0.062 g). $^1$H NMR δ (methanol-d4): 1.77-2.00 (2H, m), 2.15-2.45 (6H, m), 3.0 (3H, s), 3.07-3.25 (2H, m), 3.45-3.85 (6H, m), 4.28-4.39 (1H, m), 7.67-7.69 (2H, d, J=8 Hz), 7.90-7.88 (2H, d, J=8 Hz), 8.25 (1H, d, J=8 Hz), 8.42 (1H, d, J=8 Hz), 8.99 (1H, d, J=1.2 Hz). LCMS electrospray (+ve) 393 (MH$^+$).

EXAMPLE 14

5-{4-[(4-Cyclobutylhexahydro-1H-1,4-diazepin-1-yl)carbonyl]phenyl}-2-cyanopyridine hydrochloride (E14)

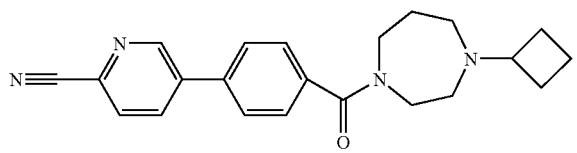

The title compound (E14) was prepared in a similar manner to Example 11 from 5-bromo-2-cyanopyridine (0.043 g) and 1-cyclobutyl-4-{[4-(4,4,5,5-tetramethyl-1,3,2-dioxaborolan-2-yl)phenyl]carbonyl}hexahydro-1H-1,4-diazepine (D7) (0.1 g). $^1$H NMR δ (methanol-d4): 1.8-1.9 (2H, m), 2.18-2.38 (6H, m), 3.05-3.20 (2H, m), 3.48-3.90 (6H, m), 4.28-4.38 (1H, m), 7.64 (2H, d, J=8.4 Hz), 7.83 (2H, d, J=8.4 Hz), 7.92 (1H, d, J=8 Hz), 8.24 (1H, dd, J=8 Hz), 9.04 (1H, d, J=1.6 Hz). LCMS electrospray (+ve) 361 (MH$^+$).

EXAMPLE 15

5-(4-{[4-(1-Isopropyl)hexahydro-1H-1,4-diazepin-1-yl]carbonyl}phenyl)-2-cyanopyridine hydrochloride (E15)

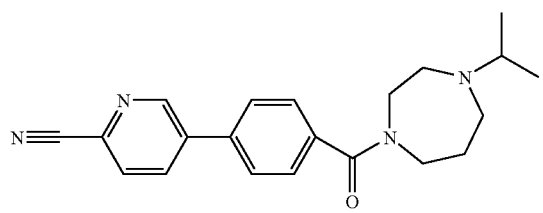

4-(6-Cyano-3-pyridinyl)benzoic acid (D9) (0.35 g) was dissolved in dry DMF and treated with EDC (0.51 g) and a catalytic quantity of HOAT. The reaction mixture was stirred at rt for 5 min, followed by the addition of 1-(isopropyl)-hexahydro-1H-1,4-diazepine dihydrochloride (D2) (0.28 g) and N,N-diisopropylethylamine (1 ml), and allowed to stir at rt overnight. After evaporation of solvent the residue was partitioned between DCM (15 ml) and water (15 ml). The DCM layer was dried (magnesium sulfate) and concentrated to leave a crude residue which was purified by flash chromatography [silica gel, step gradient 0-15% MeOH (containing 10% 0.88 ammonia solution) in DCM]. Pure fractions were combined and concentrated to give the free base which was converted into the HCl salt in DCM (2 ml) with 1N ethereal HCl (1 ml). Evaporation of the solvents afforded the title compound (E15) (8 mg). $^1$H NMR δ (methanol-d4): 1.4 (6H, d, J=6.4 Hz), 2.16 (2H, bs), 3.47-4.2 (8H, m), 4.2-4.4 (1H, m), 7.68 (2H, d, J=8 Hz), 7.85 (2H, d, J=8 Hz), 7.98 (1H, d, J=8 Hz), 8.29 (1H, dd, J=8 Hz), 9.04 (1H, d, J=1.6 Hz). LCMS electrospray (+ve) 349 (MH$^+$).

EXAMPLE 16

N-Methyl-5-(4-{[4-(1-isopropyl)hexahydro-1H-1,4-diazepin-1-yl]carbonyl}phenyl)-2-pyridinecarboxamide hydrochloride (E16)

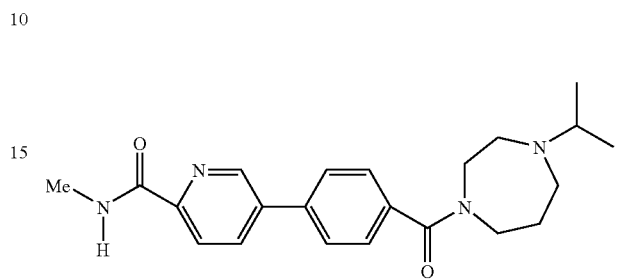

The title compound (E16) was prepared in a similar manner to Example 11 from 1-(isopropyl)-4-{([4-(4,4,5,5-tetramethyl-1,3,2-dioxaborolan-2-yl)phenyl]carbonyl}hexahydro-1H-1,4-diazepine (D12) (0.15 g) and 5-bromo-N-methyl-2-pyridine carboxamide (D11) (0.086 g). After SCX work-up the product was purified using flash chromatography [silica gel, step gradient 0-15% MeOH (containing 10% 0.88 ammonia solution) in DCM]. The free base product was dissolved in dry DCM (2 ml) and treated with 1N ethereal HCl (1 ml). Evaporation of solvents afforded the title compound (E16) as a white solid (0.1 g). $^1$H NMR δ (DMSO-d6): 1.25-1.30 (6H, m), 1.99-2.2 (1H, m), 2.27-2.45 (1H, m), 2.84-2.85 (3H, d, J=4.8 Hz), 3.2-4.18 (9H, m), 7.65 (2H, d, J=8 Hz), 7.90 (2H, d, J=8 Hz), 8.12 (1H, d, J=8 Hz), 8.32 (1H, dd, J=8 Hz), 8.82 (1H, q, J=4.8 Hz), 8.98 (1H, d, J=1.6 Hz). LCMS electrospray (+ve) 381 (MH$^+$).

EXAMPLES 17-21

(E17-E21)

Examples 17-21 were prepared in a similar manner to Example 11 from 1-(isopropyl)-4-{[4-(4,4,5,5-tetramethyl-1,3,2-dioxaborolan-2-yl)phenyl]carbonyl}hexahydro-1H-1,4-diazepine (D12) and the appropriate heteroaryl bromide or chloride. All compounds displayed $^1$H NMR and mass spectral data that were consistent with structure.

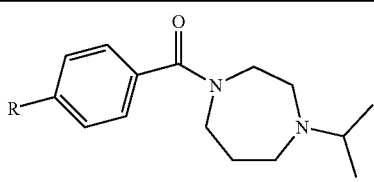

| Example No | R | Mass Spectrum (ES$^+$) |
|---|---|---|
| 17 | ![F3C-pyrimidine] | (MH+) 393 |

4.3-4.5 (1H, m), 7.72 (2H, d, J=8 Hz), 8.21 (1H, d, J=8 Hz), 8.32 (2H, d, J=8 Hz), 8.45 (1H, d, J=8 Hz).

EXAMPLE 23

1-Cyclobutyl-4-({4-[2-(trifluoromethyl)-5-pyrimidinyl]phenyl}carbonyl)hexahydro-1H-1,4-diazepine hydrochloride (E23)

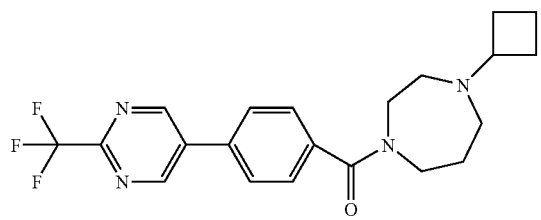

The title compound (E23) was prepared in a similar manner to Example 11 from 1-cyclobutyl-4-{[4-(4,4,5,5-tetramethyl-1,3,2-dioxaborolan-2-yl)phenyl]carbonyl}hexahydro-1H-1,4-diazepine (D7) and 5-bromo-2-trifluoromethylpyrimidine (D13). The crude product after work-up was by purified by flash chromatography [silica gel, gradient 0-100% EtOAc-MeOH] and the free base was converted into the title hydrochloride salt (E23). $^1$H NMR δ (DMSO-d6): 1.6-1.75 (2H, m), 2.0-2.4 (6H, m), 2.97-3.05 (2H, m), 3.35-3.70 (6H, m), 4.14-4.19 (1H, m), 7.67 (2H, d, J=8 Hz), 8.0 (2H, d, J=8 Hz), 9.45 (2H, s),10.8-11.0 (1H, bs). LCMS electrospray (+ve) 405 (MH$^+$).

EXAMPLE 24-28

(E24-E28)

Examples 24-28 were prepared in a similar manner to Example 15 from either 1-(cyclobutyl)hexahydro-1H-1,4-diazepine dihydrochloride (D4) or 1-(isopropyl)hexahydro-1H-1,4-diazepine dihydrochloride (D2) and the appropriate benzoic acid. The free base products were converted into the corresponding hydrochloride salts with ethereal HCl.

-continued

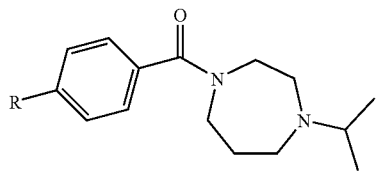

| Example No | R | Mass Spectrum (ES⁺) |
|---|---|---|
| 18 | 3-methyl-6-(trifluoromethyl)pyridazin-yl | (MH+) 393 |
| 19 | 5-methyl-2-(trifluoromethyl)pyridin-yl | (MH+) 392 |
| 20 | N,N-dimethyl-5-methylpyridine-2-carboxamide | (MH+) 395 |
| 21 | 5-cyano-6-methylpyridin-2-yl | (MH+) 349 |

EXAMPLE 22

1-Cyclobutyl-4-({4-[6-(trifluoromethyl)-3-pyridazinyl]phenyl}carbonyl)hexahydro-1H-1,4-diazepine hydrochloride (E22)

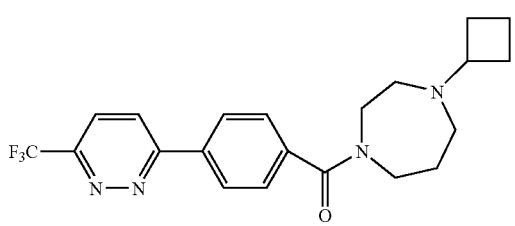

The title compound (E22) was prepared in a similar manner to Example 11 from 1-cyclobutyl-4-{[4-(4,4,5,5-tetramethyl-1,3,2-dioxaborolan-2-yl)phenyl]carbonyl}hexahydro-1H-1,4-diazepine (D7) and 3-chloro-6-(trifluoromethyl)pyridazine (Goodman, Stanforth and Tarbit, Tetrahedron, 1999, 55, 15067). The crude product after work-up was by purified by flash chromatography [silica gel, gradient 0-100% EtOAc-MeOH] and the free base was converted into the title hydrochloride salt (E22). $^1$H NMR δ (methanol-d4): 1.8-1.95 (2H, m), 2.15-2.48 (6H, m), 3.07-3.25 (2H, m), 3.48-3.95 (6H, m),

| Example No | R | R¹ | Mass Spectrum |
|---|---|---|---|
| 24 | 3-methylbenzamide (H₂N-C(O)-) | cyclobutyl | [MH]⁺ 378 (ES⁺) |

-continued

Structure: 4-R-benzoyl group attached to hexahydro-1H-1,4-diazepine with N-R¹

| Example No | R | R¹ | Mass Spectrum |
|---|---|---|---|
| 25 | 3-CF₃, 4-CN, 1-methyl-pyrazol-5-yl | cyclobutyl | [MH]⁺ 418 (ES⁺) |
| 26 | 5-CF₃-1-ethyl-2-oxo-pyridin-3-yl | cyclobutyl | [MH]⁺ 434 (ES⁺) |
| 27 | 4-NC-phenyl | isopropyl | [MH]⁺ 348 (APCI) |
| 28 | 4,6-dimethyl-2-(dimethylamino)pyrimidin-5-yl | cyclobutyl | [MH]⁺ 394 (ES⁺) |

EXAMPLE 29-43

(E29-E43)

Examples 29-43 were prepared from either 1-(cyclobutyl)hexahydro-1H-1,4-diazepine dihydrochloride (D4) (0.19) or 1-(isopropyl)hexahydro-1H-1,4-diazepine dihydrochloride (D2) (0.1 g) in a 1:1 mixture of DCM/DMF (5 ml). To this solution diethylaminomethyl-polystyrene (3.2 mmole/g) (0.4 g, 3 eq) was added and stirred at rt for 10 min, followed by the addition of N-cyclohexylcarbodiimide-N-methylpolystyrene (200-400 mesh, 2.3 mmole/g) (0.2 g), catalytic HOBT and 1 equivalent of the appropriate benzoic acid. The reaction mixture was shaken at rt for 48 h. Tris-(2-aminoethyl) aminomethyl polystyrene (PS-Trisamine) (0.050 g) was added and the reaction mixture was shaken at rt for further 4 h. The resins were filtered off and the filtrate was evaporated to dryness. The crude residue was purified by flash chromatography [silica gel, step gradient 0-15% MeOH (containing 10% 0.88 ammonia solution) in DCM]. The free base compounds were converted into the HCl salts in dry DCM (2 ml) with ethereal HCl (1 ml), 1N). Compounds showed ¹H NMR and mass spectra that were consistent with structure.

| Example No | R | R¹ | Mass Spectrum |
|---|---|---|---|
| E29 | 4-F-phenyl | cyclobutyl | [MH]⁺ 353 (APCI) |
| E30 | 3-F-phenyl | cyclobutyl | [MH]⁺ 353 (APCI) |
| E31 | pyridin-2-yl | cyclobutyl | [MH]⁺ 336 (ES⁺) |
| E32 | pyridin-3-yl | cyclobutyl | [MH]⁺ 336 (ES⁺) |
| E33 | 4-NC-2-methoxy-phenyl | cyclobutyl | [MH]⁺ 376 (ES⁺) |
| E34 | 4-ethoxy-phenyl (phenyl-O-Et) | cyclobutyl | [MH]⁺ 365 (APCI) |
| E35 | 3,4,5-trimethyl-isoxazol-4-yl | cyclobutyl | [MH]⁺ 354 (APCI) |
| E36 | 3,4,5-trimethyl-isoxazol-4-yl | isopropyl | [MH]⁺ 342 (APCI) |
| E37 | oxazol-5-yl | cyclobutyl | [MH]⁺ 326 (ES⁺) |
| E38 | 2-ethyl-2H-tetrazol-5-yl | cyclobutyl | [MH]⁺ 355 (APCI) |
| E39 | 1-methyl-pyrrol-2-yl | cyclobutyl | [MH]⁺ 324 (ES⁺) |

-continued

Structure: 4-R-benzoyl-hexahydro-1,4-diazepine with N-R¹

| Example No | R | R¹ | Mass Spectrum |
|---|---|---|---|
| E40 | 1,3-dimethyl-1H-pyrazol-4-yl (Me, N-Me, Me) | cyclobutyl | [MH]⁺ 353 (APCI) |
| E41 | 3,5-dimethyl-1H-pyrazol-4-yl | 1-(cyclobutyl)ethyl | [MH]⁺ 367 (APCI) |
| E42 | morpholinomethyl | cyclobutyl | [MH]⁺ 344 (ES⁺) |
| E43 | morpholinomethyl | isopropyl | [MH]⁺ 332 (ES⁺) |

EXAMPLES 44-51

(E44-E51)

Examples 44-51 were prepared in a similar manner to Examples 29-43 from 1-(cyclobutyl)hexahydro-1H-1,4-diazepine dihydrochloride (D4) and the appropriate benzoic acid.

Structure: 3-R-benzoyl-4-cyclobutyl-hexahydro-1,4-diazepine

| Example No | R | Mass Spectrum |
|---|---|---|
| E44 | benzyloxymethyl (PhCH₂OCH₂–) | [MH]⁺ 365 (APCI) |
| E45 | (pyridin-3-ylmethoxy)methyl | [MH]⁺ 366 (APCI) |
| E46 | (pyrazin-2-yl)methoxymethyl | [MH]⁺ 367 (APCI) |
| E47 | 1,5-dimethyl-1H-tetrazol-2-yl | [MH]⁺ 341 (APCI) |
| E48 | 1-methyl-2-oxopyrrolidin-3-yl | [MH]⁺ 342 (APCI) |
| E49 | N-methylnicotinamide (pyridin-3-yl C(O)NHMe) | [MH]⁺ 379 (ES⁺) |
| E50 | N-methylisonicotinamide (pyridin-4-yl C(O)NHMe) | [MH]⁺ 379 (ES⁺) |
| E51 | 5-methylpyridin-3-yl | [MH]⁺ 336 (ES⁺) |

EXAMPLES 52-55

(E52-E55)

Examples 52-55 were prepared in a similar manner to Example 11 from 1-cyclobutyl-4-{[4-(4,4,5,5-tetramethyl-1,3,2-dioxaborolan-2-yl)phenyl]carbonyl}hexahydro-1H-1,4-diazepine (D7) and the appropriate aryl bromides (e.g. D14-D16 for E53-E55, respectively), except that THF/H₂O was used as solvent and potassium carbonate as base, and the reaction was heated at 80-85° C. for 1 h. Compounds showed ¹H NMR and mass spectra that were consistent with structure.

| Example No | R | Mass Spectrum |
|---|---|---|
| E52 | oxazol-2-yl (linked via 2-position) | [MH]+ 402 (ES+) |
| E53 | 2-methyl-oxazol-4-yl | [MH]+ 416 (ES+) |
| E54 | 2-methyl-oxazol-5-yl | [MH]+ 416 (ES+) |
| E55 | 5-methyl-1,2,4-oxadiazol-3-yl | [MH]+ 417 (ES+) |

EXAMPLE 56

1-Cyclobutyl-4-{[4-(1,3-oxazol-2-yl)phenyl]carbonyl}hexahydro-1H-1,4-diazepine hydrochloride (E56)

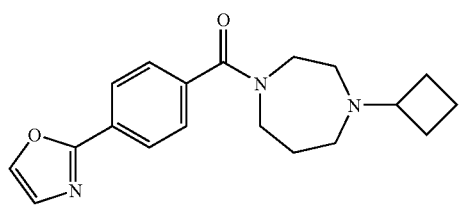

Step 1: 1,1-Dimethylethyl 4-([4-(1,3-oxazol-2-yl)phenyl]carbonyl)hexahydro-1H-1,4-diazepine carboxylate A microwave vial was charged with 2-(4-bromophenyl)-oxazole (D17) (0.224 g), molybdenum hexacarbonyl (0.111 g), trans-Di-μ-acetatobis[2-(di-o-tolylphosphino)benzyl]palladium(II) (0.04 g), (±)-2,2'-bis(diphenylphosphino)-1,1'-binaphthyl (0.08 g) and purged with argon. Diglyme (4 ml), toluene (2 ml) and 4M aqueous potassium carbonate (0.74 ml) were added, and the reaction mixture was degassed by argon saturation. tert-Butyl-hexahydro-1H-1,4-diazepine carboxylate (0.22 g) was added and the reaction vial was heated at 150° C. for 20 min in the microwave reactor. The reaction mixture was filtered, dried ($Na_2SO_4$) and evaporated. Chromatography of the crude product (silica gel, eluting with EtOAc/hexanes, 50-100%) afforded the subtitle compound (0.141 g).

Step 2: 4-{[4-(1,3-Oxazol-2-yl)phenyl]carbonyl}hexahydro-1H-1,4-diazepine

The product from E56, Step 1 was dissolved in DCM (5 ml) and TFA (0.5 ml) was added. After 7 h saturated aqueous potassium carbonate (5 ml) was added and the aqueous phase extracted into DCM (3×10 ml). The combined organics were washed with brine (20 ml), dried ($MgSO_4$) and evaporated to give the subtitle compound as a yellow oil (0.064 g).

Step 3: 1-Cyclobutyl-4-{[4-(1,3-oxazol-2-yl)phenyl]carbonyl}hexahydro-1H-1,4-diazepine hydrochloride Cyclobutanone (0.04 ml) was added to a solution of the product of E56 Step 2 (0.064 g) and triethylamine (0.12 ml) in DCM (2.5 ml). After 5 min sodium triacetoxyborohydride (0.111 g) was added and the reaction mixture was stirred for 16 h. Saturated aqueous sodium hydrogen carbonate (5 ml) was added and the aqueous phase extracted into DCM (10 ml). The organic phase was filtered through a PhaseSep® cartridge and evaporated. Chromatography of the crude mixture [silica gel, eluting with 2N $NH_3$ in MeOH/DCM, 0-15%] afforded the required amine free base, which was dissolved in DCM (2 ml) and treated with HCl (1 ml), 1M in diethyl ether). The precipitate was filtered and dried to give the title compound (E56) (0.07 g). MS electrospray (+ion) 326 (MH+).

EXAMPLE 57

1-(1-Methylethyl)-4-{[4-(3-methyl-1,2,4-oxadiazol-5-yl)phenyl]carbonyl}hexahydro-1H-1,4-diazepine hydrochloride

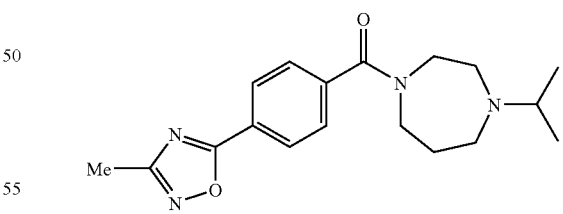

4-(3-Methyl-1,2,4-oxadiazol-5-yl)benzoic acid (D18) (0.415 g), 1-(isopropyl)hexahydro-1H-1,4-diazepine (free base of D2) (0.294 g), EDC (0.425 g) and HOBT (0.282 g) were dissolved in DMF (10 ml) and stirred under argon. Hunig's base (1.43 ml) was added and the reaction mixture stirred for 15 h. The solvent was evaporated and the yellow residue partitioned between DCM (10 ml) and saturated sodium hydrogen carbonate (10 ml). The aqueous phase was extracted into DCM (2×10 ml), dried ($MgSO_4$) and evaporated to give the crude amide as a brown solid. Chromatography of the crude mixture [silica gel, eluting with MeOH/DCM, 0-20%] afforded the desired amine free base, which was dissolved in DCM (2 ml) and treated with HCl (1 ml), 1M in diethyl ether). The precipitate was filtered and dried to give the title compound (E57) (0.07 g). MS electrospray (+ion) 329 (MH$^+$). $^1$H NMR δ (CDC$_{13}$, free base): 8.16 (2H, d, J=8.4 Hz), 7.56 (2H, d, J=8.4 Hz), 3.79-3.77 (2H, m), 3.44-3.40 (2H, m), 2.93 (1H, app pent, J=6.8 Hz), 2.82 (1H, app tr, J=5.2 Hz), 2.70 (1H, app tr, J=5.8 Hz), 2.65-2.59 (2H, m), 2.48 (3H, s), 1.96-1.90 (1H, m), 1.77-1.71 (1H, m), 1.04 (3H, d, J=6.4 Hz) and 0.99 (3H, d, J=6.4 Hz).

EXAMPLE 58

1-Cyclobutyl-4-{[4-(3-methyl-1,2,4-oxadiazol-5-yl)phenyl]carbonyl}hexahydro-1H-1,4-diazepine hydrochloride (E58)

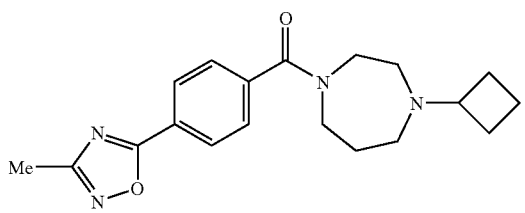

4-(3-Methyl-1,2,4-oxadiazol-5-yl)benzoic acid (D18) (0.365 g), 1-(cyclobutyl)hexahydro-1H-1,4-diazepine free base compound from D4) (0.28 g), EDC (0.374 g) and HOBT (0.248 g) were dissolved in DMF (10 ml) and stirred under argon. Hunig's base (1.26 ml) was added and the reaction mixture stirred for 15 h. The solvent was evaporated and the yellow residue partitioned between DCM (10 ml) and saturated sodium hydrogen carbonate (10 ml). The aqueous phase was extracted into DCM (2×10 ml), dried (MgSO$_4$) and evaporated to give the crude amide as a brown solid. Chromatography of the crude mixture [silica gel, eluting with MeOH/DCM, 0-20%] afforded the desired amine free base, which was dissolved in DCM (2 ml) and treated with HCl (1 ml), 1M in diethyl ether). The precipitate was filtered and dried to give the title compound (E58) (0.07 g). MS electrospray (+ion) 341 (MH$^+$). $^1$H NMR δ (CDCl$_3$, free base): 8.16 (2H, d, J=8.4 Hz), 7.55 (2H, d, J=8.4 Hz), 3.81-3.78 (2H, m), 3.48-3.42 (2H, m), 2.97-2.85 (1H, m), 2.65-2.63 (1H, m), 2.54-2.42 (3H, m), 2.50 (3H, s), 2.11-1.95 (3H, m), 1.90-1.75 (3H, m) and 1.71-1.58 (2H, m).

| Abbreviations | |
|---|---|
| Boc | tert-butoxycarbonyl |
| EtOAc | ethyl acetate |
| h | hour |
| min | minutes |
| DCM | dichloromethane |
| MeOH | methanol |
| rt | room temperature |
| DMF | dimethylformamide |
| TFA | trifluoroacetic acid |
| HOBT | 1-hydroxybenzotriazole |
| EDC | 1-(3-dimethylaminopropyl)-3-ethylcarbodiimide hydrochloride |

All publications, including but not limited to patents and patent applications, cited in this specification are herein incorporated by reference as if each individual publication were specifically and individually indicated to be incorporated by reference herein as though fully set forth.

Biological Data

A membrane preparation containing histamine H3 receptors may be prepared in accordance with the following procedures:

(i) Generation of Histamine H3 Cell Line

DNA encoding the human histamine H3 gene (Huvar, A. et al. (1999) Mol. Pharmacol. 55(6), 1101-1107) was cloned into a holding vector, pCDNA3.1 TOPO (InVitrogen) and its cDNA was isolated from this vector by restriction digestion of plasmid DNA with the enzymes BamH1 and Not-1 and ligated into the inducible expression vector pGene (InVitrogen) digested with the same enzymes. The GeneSwitch™ system (a system where in transgene expression is switched off in the absence of an inducer and switched on in the presence of an inducer) was performed as described in U.S. Pat. Nos. 5,364,791; 5,874,534; and 5,935,934. Ligated DNA was transformed into competent DH5α *E. coli* host bacterial cells and plated onto Luria Broth (LB) agar containing Zeocin™ (an antibiotic which allows the selection of cells expressing the sh ble gene which is present on pGene and pSwitch) at 50 μg ml$^{-1}$. Colonies containing the re-ligated plasmid were identified by restriction analysis. DNA for transfection into mammalian cells was prepared from 250 ml) cultures of the host bacterium containing the pGeneH3 plasmid and isolated using a DNA preparation kit (Qiagen Midi-Prep) as per manufacturers guidelines (Qiagen).

CHO K1 cells previously transfected with the pSwitch regulatory plasmid (InVitrogen) were seeded at 2×10 e6 cells per T75 flask in Complete Medium, containing Hams F12 (GIBCOBRL, Life Technologies) medium supplemented with 10% v/v dialysed foetal bovine serum, L-glutamine, and hygromycin (100 μg ml$^{-1}$), 24 hours prior to use. Plasmid DNA was transfected into the cells using Lipofectamine plus according to the manufacturers guidelines (InVitrogen). 48 hours post transfection cells were placed into complete medium supplemented with 500 μg ml$^{-1}$ Zeocin™.

10-14 days post selection 10 nM Mifepristone (InVitrogen), was added to the culture medium to induce the expression of the receptor. 18 hours post induction cells were detached from the flask using ethylenediamine tetra-acetic acid (EDTA; 1:5000; InVitrogen), following several washes with phosphate buffered saline pH 7.4 and resuspended in Sorting Medium containing Minimum Essential Medium (MEM), without phenol red, and supplemented with Earles salts and 3% Foetal Clone II (Hyclone). Approximately 1×10 e7 cells were examined for receptor expression by staining with a rabbit polyclonal antibody, 4a, raised against the N-terminal domain of the histamine H3 receptor, incubated on ice for 60 minutes, followed by two washes in sorting medium. Receptor bound antibody was detected by incubation of the cells for 60 minutes on ice with a goat anti rabbit antibody, conjugated with Alexa 488 fluorescence marker (Molecular Probes). Following two further washes with Sorting Medium, cells were filtered through a 50 μm Filcon™ (BD Biosciences) and then analysed on a FACS Vantage SE Flow Cytometer fitted with an Automatic Cell Deposition Unit. Control cells were non-induced cells treated in a similar manner. Positively stained cells were sorted as single cells into 96-well plates, containing Complete Medium containing 500 μg ml$^{-1}$ Zeocin™ and allowed to expand before reanalysis for receptor expression via antibody and ligand binding studies. One clone, 3H3, was selected for membrane preparation.

(ii) Membrane Preparation from Cultured Cells

All steps of the protocol are carried out at 4° C. and with pre-cooled reagents. The cell pellet is resuspended in 10 volumes of buffer A2 containing 50 mM N-2-hydroxyethylpiperazine-N'-2-ethanesulfonic acid (HEPES) (pH 7.40) supplemented with 10 e-4M leupeptin (acetyl-leucyl-leucyl-arginal; Sigma L2884), 25 µg/ml bacitracin (Sigma B0125),1 mM ethylenediamine tetra-acetic acid (EDTA), 1 mM phenylmethylsulfonyl fluoride (PMSF) and 2×10 e-6M pepstain A (Sigma). The cells are then homogenised by 2×15 second bursts in a 1 litre glass Waring blender, followed by centrifugation at 500 g for 20 minutes. The supernatant is then spun at 48,000 g for 30 minutes. The pellet is resuspended in 4 volumes of buffer A2 by vortexing for 5 seconds, followed by homogenisation in a Dounce homogeniser (10-15 strokes). At this point the preparation is aliquoted into polypropylene tubes and stored at −70° C.

(iii) Generation of Histamine H1 Cell Line

The human H1 receptor was cloned using known procedures described in the literature [Biochem. Biophys. Res. Commun. 1994, 201(2), 894]. Chinese hamster ovary cells stably expressing the human H1 receptor were generated according to known procedures described in the literature [Br. J. Pharmacol. 1996, 117(6), 1071].

Compounds of the invention may be tested for in vitro biological activity in accordance with the following assays:

(I) Histamine H3 Binding Assay

For each compound being assayed, in a white walled clear bottom 96 well plate, is added:

(a) 10 µl of test compound (or 10 µl of iodophenpropit (a known histamine H3 antagonist) at a final concentration of 10 mM) diluted to the required concentration in 10% DMSO;

(b) 10 µl $^{125}$I 4-[3-(4-iodophenylmethoxy)propyl]-1H-imidazolium (iodoproxyfan) (Amersham; 1.85MBq/µl or 50 µCi/ml; Specific Activity ~2000 Ci/mmol) diluted to 200 pM in assay buffer (50 mM Tris(hydroxymethyl)aminomethane buffer (TRIS) pH 7.4, 0.5mM ethylenediamine tetra-acetic acid (EDTA)) to give 20 pM final concentration; and (c) 80 µl bead/membrane mix prepared by suspending Scintillation Proximity Assay (SPA) bead type WGA-PVT at 100 mg/ml in assay buffer followed by mixing with membrane (prepared in accordance with the methodology described above) and diluting in assay buffer to give a final volume of 80 µl which contains 7.5 µg protein and 0.25 mg bead per well-mixture was pre-mixed at room temperature for 60 minutes on a roller. The plate is shaken for 5 minutes and then allowed to stand at room temperature for 3-4 hours prior to reading in a Wallac Microbeta counter on a 1 minute normalised tritium count protocol. Data was analysed using a 4-parameter logistic equation.

(II) Histamine H3 Functional Antagonist Assay

For each compound being assayed, in a white walled clear bottom 96 well plate, is added:

(a) 10 µl of test compound (or 10 µl of guanosine 5'-triphosphate (GTP) (Sigma) as non-specific binding control) diluted to required concentration in assay buffer (20 mM N-2-Hydroxyethylpiperazine-N'-2-ethanesulfonic acid (HEPES)+100 mM NaCl+10 mM MgCl$_2$, pH7.4 NaOH);

(b) 60 µl bead/membrane/GDP mix prepared by suspending wheat germ agglutinin-polyvinyltoluene (WGA-PVT) scintillation proximity assay (SPA) beads at 100 mg/ml in assay buffer followed by mixing with membrane (prepared in accordance with the methodology described above) and diluting in assay buffer to give a final volume of 60 µl which contains 100 µg protein and 0.5 mg bead per well-mixture is pre-mixed at 4° C. for 30 minutes on a roller and just prior to addition to the plate, 10 µM final concentration of guanosine 5' diphosphate (GDP) (Sigma; diluted in assay buffer) is added; The plate is incubated at room temperature to equilibrate antagonist with receptor/beads by shaking for 30 minutes followed by addition of:

(c) 10 µl histamine (Tocris) at a final concentration of 0.3 µM; and (d) 20 gl guanosine 5'[γ35-S] thiotriphosphate, triethylamine salt (Amersham; radioactivity concentration=37 kBq/µl or 1 mCi/ml; Specific Activity 1160 Ci/mmol) diluted to 1.9nM in assay buffer to give 0.38nM final.

The plate is then incubated on a shaker at room temperature for 30 minutes followed by centrifugation for 5 minutes at 1500 rpm. The plate is read between 3 and 6 hours after completion of centrifuge run in a Wallac Microbeta counter on a 1 minute normalised tritium count protocol. Data is analysed using a 4-parameter logistic equation. Basal activity used as minimum i.e. histamine not added to well.

(III) Histamine H1 Functional Antagonist Assay

Compounds are assayed in a black walled clear bottom 384-well plate with cells seeded at 10000 cells/well. Tyrodes buffer is used throughout (NaCl 145 mM, KCl 2.5 mM, HEPES 10 mM, glucose 10 mM, MgCl$_2$ 1.2 mM, CaCl$_2$ 1.5 mM, probenecid 2.5 mM, pH adjusted to 7.40 with NaOH 1.0 M). Each well is treated with 10 µl of a solution of FLUO4AM (10 µM in Tyrodes buffer at pH 7.40) and plates are then incubated for 60 minutes at 37° C. Wells are then washed with Tyrodes buffer using a EMBLA cell washer system, leaving 40 µl buffer in each well, and then treated with 10 µl of test compound in Tyrodes buffer. Each plate is incubated for 30 min to allow equilibration of the test compound with the receptor. Each well is then treated with 10 µl of histamine solution in Tyrodes buffer.

Functional antagonism is indicated by a suppression of histamine induced increase in fluorescence, as measured by the FLIPR system (Molecular Devices). By means of concentration effect curves, functional potencies are determined using standard pharmacological mathematical analysis.

Results

The compounds of Examples E1-E58 were tested in the histamine H3 functional antagonist assay and exhibited pK$_b$ values>8.0. More particularly, the compounds of Examples 1-9, 11-14, 16, 22-28, 30-42, 44, 47, 52-56 and 58 exhibited pK$_b$ values≧9.0. Most particularly, the compounds of Examples 1, 2, 11, 12 and 58 exhibited pK$_b$ values>9.5.

The compounds of Examples E1 42, 44, 46-48 and 51-55 were tested in the histamine H1 functional antagonist assay and exhibited antagonism<7.0 pK$_b$. More particularly, the compounds of Examples E1-25, 27-42, 44, 46-48 and 51-55 exhibited antagonism<6.0 pK$_b$.

The invention claimed is:

1. A compound which is 1-(isopropyl)-4-{[4-(tetrahydro-2H-pyran4-yloxy)phenyl]carbonyl}hexahydro-1H-1,4-diazepine:

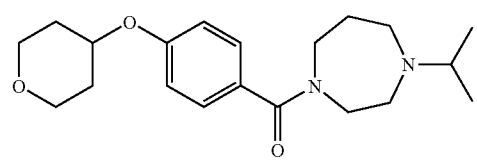

or a pharmaceutically acceptable salt thereof.

2. A compound according to claim 1 which is 1-(isopropyl)-4-{[4-(tetrahydro-2H-pyran-4-yloxy)phenyl]carbonyl}hexahydro-1H-1,4diazepine hydrochloride.

3. A pharmaceutical composition which comprises the compound of claim 1 or a pharmaceutically acceptable salt thereof and a pharmaceutically acceptable carrier or excipient.

4. A method of treatment of neurological diseases which comprises administering to a host in need thereof an effective amount of the compound of claim 1 or a pharmaceutically acceptable salt thereof, which neurological diseases are selected from the group consisting of Alzheimer's disease, mild cognitive impairment, and cognitive deficit.

* * * * *